(12) United States Patent
Chen et al.

(10) Patent No.: US 12,392,772 B2
(45) Date of Patent: Aug. 19, 2025

(54) METHOD FOR DETECTION AND SEPARATION OF ENANTIOMERS USING VESICLE-LIKE NANOSTRUCTURES SELF-ASSEMBLED FROM JANUS NANOPARTICLES

(71) Applicant: The Regents of the University of California, Oakland, CA (US)

(72) Inventors: Shaowei Chen, Santa Cruz, CA (US); Jia-En Lu, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 1202 days.

(21) Appl. No.: 16/975,604

(22) PCT Filed: Feb. 14, 2019

(86) PCT No.: PCT/US2019/017926
§ 371 (c)(1),
(2) Date: Aug. 25, 2020

(87) PCT Pub. No.: WO2019/164734
PCT Pub. Date: Aug. 29, 2019

(65) Prior Publication Data
US 2020/0400660 A1    Dec. 24, 2020

Related U.S. Application Data

(60) Provisional application No. 62/635,217, filed on Feb. 26, 2018.

(51) Int. Cl.
G01N 33/543  (2006.01)
G01N 21/19   (2006.01)

(52) U.S. Cl.
CPC ....... *G01N 33/54346* (2013.01); *G01N 21/19* (2013.01)

(58) Field of Classification Search
None
See application file for complete search history.

(56) References Cited

U.S. PATENT DOCUMENTS

| | | | |
|---|---|---|---|
| 8,062,893 B2 * | 11/2011 | Wang | G01N 33/1813 436/81 |
| 2010/0009344 A1 * | 1/2010 | Israel | B82Y 30/00 435/5 |

(Continued)

OTHER PUBLICATIONS

Di ("Anionic surfactant templated chiral nanospheres and their enantioselective adsorption," Di, et al., New J. Chem, 2013) (Year: 2013).*

(Continued)

*Primary Examiner* — Uzma Alam
*Assistant Examiner* — Chad Andrew Reverman
(74) *Attorney, Agent, or Firm* — Carter, DeLuca & Farrell LLP (57) ABSTRACT

A method for processing an analyte includes: adding a plurality of amphiphilic nanoparticles to a solvent to form a mixture having a plurality of enantioselective nanoparticle ensembles; adding an analyte to the mixture; obtaining a test circular dichroism spectrum of the mixture with the analyte; and determining an enantiomeric property of the analyte based on a comparison of a baseline circular dichroism spectrum of the analyte mixture to the test circular dichroism spectrum.

14 Claims, 8 Drawing Sheets

(56) References Cited

U.S. PATENT DOCUMENTS

2016/0145558 A1* 5/2016 Boedicker .............. C12P 39/00
435/289.1
2018/0356414 A1* 12/2018 Strano ................ G01N 33/5308

OTHER PUBLICATIONS

Song ("Janus Nanoparticles as Versatile Phase-Transfer Reagents," Song, et al., American Chemical Society, 2014) (Year: 2014).*
Zhang ("Colorimetric Chiral Recognition of Enantiomers Using the Nucleotide-Capped Silver Nanoparticles," Zhang, et al., American Chemical Society, 2011) (Year: 2011).*
Fernandes ("Assessment of Mixed Monolayer-protected Gold Nanoparticles Assembly in Solution: Study and Characterization," Fernandes, Imperial College London, 2010) (Year: 2010).*
Cecchini ("Self-assembled nanoparticle arrays for multiphase trace analyte detection," Cecchini, et al., Nature Materials, 2013) (Year: 2013).*
Mendez-Gonzalez ("Multi-responsive hybrid Janus nanoparticles: Surface functionalization through solvent physisorption," Mendez-Gonzalez et al., European Polymer Journal, Feb. 2016, https://www.sciencedirect.com/science/article/pii/S0014305716300131) (Year: 2016).*
Allenmark, Stig, "Induced Circular Dichroism by Chiral Molecular Interaction", Department of Chemistry, Goteborg University, Chirality, 2003, vol. 15, pp. 409-422.
Baumruk, Vladimir, et al., "Predictions of Secondary Structure Using Statistical Analyses of Electronic and Vibrational Circular Dischroism and Fourier Transform Infrared Spectra of Proteins in H2O", J. Mol. Biol. (1996) vol. 259, pp. 774-791.
Ben-Moshe, Assaf et al., "Probing the Interation of Quantum Dots with Chiral Capping Molecules Using Circular Dischrioism Spectroscopy", ACS Publications, Nano Letters, 2016, vol. 16, pp. 7467-7473.
Berova, Nina et al., "Application of Electronic Circular Dichroism in Configurational and Conformational Analysis of Organic Compounds", Chem. Soc. Rev., vol. 2007, 36, pp. 914-931.
Chen, Huaiya, et al., "Optically Active Helical Polyacetylene/ Fe3O4 Composite Microspheres: Prepared by Precipitation Polymerization and Used for Enantioselective Crystallization", Royal Society of Chemistry, 2014, vol. 4, pp. 63611-63619.
Chinta, Jugan Prakash, "Coinage Metal Nanoparticles Based Colorimetric assays for Natural Amino Acids: A Review of Recent Developments", Sensors and Actuators B, 2017, vol. 248, pp. 733-452.
DeVries, Gretchen A., et al., "Divalent Metal Nanoparticles", Science Magazine, 2007, vol. 315, pp. 358-362.
DiGregorio, Maria C. et al., "Chiroptical Study of Plasmon—Molecule Interaction: The Case of Interaction of Glutathione with Silver Nanocubes", The Journal of Physical Chemistry, 2015, vol. 119, pp. 17111-17116.
Droulias, Sotiris, et al., "Broad-Band Giant Circular Dichroism in Metamaterials of Twisted Chains of Metallic Nanoparticles", The Journal of Physical Chemistry, 2013, vol. 117, pp. 1130-1135.
Esposito, Marco, et al., Triple-Helical Nanowires by Tomographic Rotatory Growth for Chiral Photonics, Nature Communications, Published Mar. 18, 2015, pp. 1-7.
Esposito,M. et al., "Programmable Extreme Chirality in the Visible by Helix-Shaped Metamaterial Platform", Nano Letters, 2016, vol. 16, pp. 5823-5828.
Fan, Z. et al., "Plasmonic Circular Dichroism of Chiral Metal Nanoparticle Assemblies", Nano Letters, 2010, vol. 10, pp. 2580-2587.
Fan, Z. et al., "Helical Metal Nanoparticle Assemblies with Defects: Plasmonic Chirality and Circular Dichroism", The Journal of Physical Chemistry, 2011, vol. 115, pp. 13524-13261.
Fan, Z. et al., "Chiral Nanocrystals: Plasmonic Spectra and Circular Dichroism", Nano Letters, 2012, vol. 12, pp. 3283-3289.

Frank, B. et al., "Large-Area 3D Chiral Plasmonic Structures", American Chemical Society, 2013, vol. 7, pp. 6321-6329.
Gautier, C., et al., "Vibrational Circular Dichroism of N-acetyl-L-cysteine Protected Gold Nanoparticles", The Royal Society of Chemistry, Chem. Commun., 205, pp. 5393-5395.
Gellman, A., "Superenantioselective Chiral Surface Explosions", Journal of the American Chemical Society, 2013, vol. 135, pp. 19208-19214.
Ghosh, S., "Interparticle Coupling Effect on the Surface Plasmon Resonance of Gold Nanoparticles: From Theory to Applications", American Chemical Society, 2007, vol. 107, pp. 4797-4862.
Govorov, A., "Plasmon-Induced Circular Dichroism of a Chiral Molecule in the Vicinity of Metal Nanocrystals. Application to Various Geometries", The Journal of Physical Chemistry, 2011, vol. 115, pp. 7914-7923.
Govorov, A., "Chiral Nanoparticle Assemblies: Circular Dichroism, Plasmonic Interactions, and Exciton Effects", Journals of Materials Chemistry, 2011, vol. 21, pp. 16806-16818.
Hildalgo, F., "First-Principles Calculations of Circular Dichroism of Ligand-Protected Gold Nanoparticles", The European Physical Journal D, 2009, pp. 179-182.
Hildago, F., Metallic Influence on the Atomic Structure and Optical Activity of Ligand-Protected Nanoparticles: a Comparison between Ag and Au, the Royal Society of Chemistry, Nanoscale, 2014, vol. 6, pp. 3325-3334.
Hou, S., et al., "Plasmonic Circular Dichroism in Side-by-Side Oligomers of Gold Nanorods: The Influence of Chiral Molecule Location and Interparticle Distance", Phys. Chem. Chem. Phys., 2015, vol. 17, pp. 8187-8193.
Hou, S., et al., "Enhancing the Plasmonic Circular Dichroism by Entrapping Chiral Molecules at the Core-Shell Interface of Rod-Shaped Au—Ag Nanocrystals", Chem. Commun., 2016, vol. 52, pp. 2059-2062.
Jarrett, J. et al., "Plasmon-Mediated Two-Photon Photoluminescence-Detected Circular Dichroism in Gold Nanosphere Assemblies", J. Phys. Chem. Lett., 2016, vol. 7, pp. 765-770.
Jin, X., et al., "Reversible Plasmonic Circular Dichroism via Hybrid Supramolecular Gelation of Achiral Gold Nanorods" ACS Nano, 2016, vol. 10, pp. 11179-11186.
Jung, S., et al., "Chiral Arrangement of Achiral Au Nanoparticles by Supramolecular Assembly of Helical Nanofiber Templates", J. Am. Chem. Soc., 2014, vol. 136, pp. 6446-6452.
Kumar, J., et al., "Nanoscale Chirality in Metal and Semiconductor Nanoparticles", Chem. Commun., 2016, vol. 52, pp. 12555-12569.
Kuzyk, A., et al., "DNA-Based Self-Assembly of Chiral Plasmonic Nanostructures with Tailored Optical Response", Nature, 2012, vol. 483, pp. 311-314.
Lan, X., et al., "Self-Assembly of Chiral Plasmonic Nanostructures", Advanced Materials, 2016, vol. 28, pp. 10499-10507.
Levi-Belenkova, T., et al., "Orientation-Sensitive Peptide-Induced Plasmonic Circular Dichroism in Silver Nanocubes", The Journal of Physical Chemistry, 2016, vol. 120, pp. 12751-12756.
Li, Z., et al., "Reversible Plasmonic Circular Dichroism of Au Nanorod and DNA Assemblies", J. Am. Chem. Soc., 2012, vol. 134, pp. 3322-3325.
Liu, W., "DNA Induced Intense Plasmonic Circular Dichroism of Highly Purified Gold Nanobipyramids", The Royal Society of Chemistry, 2014, vol. 6., pp. 4498-4502.
Ma, Wei, et al., "Chiral Inorganic Nanostructures", Chem. Rev., 2017, vol. 117, pp. 8041-8093.
McPeak, K. et al., "Complex Chiral Colloids and Surfaces via High-Index Off-Cut Silicon", Nano Lett., 2014, vol. 14, pp. 2934-2940.
Pradhan, S., et al., "Janus Nanoparticles by Interfacial Engineering", Adv. Funct. Mater., 2007, vol. 17, pp. 2385-2392.
Ranjbar, B., et al., "Circular Dichroism Techniques: Biomolecular and Nanostructural Analyses—A Review", Chem. Biol. Drug. Des., 2009, vol. 74, pp. 101-120.
Rao, C., et al., "Tunable Optical Activity of Plasmonic Dimers Assembled by DNA Origami", The Royal Society of Chemistry, 2015, vol. 7, pp. 9147-9152.

(56) References Cited

OTHER PUBLICATIONS

Roman-Velazquez, C., et al., "Circular Dichroism Simulated Spectra of Chiral Gold Nanoclusters: A Dipole Approximation", 2003, J. Phys. Chem. B, vol. 107, No. 44, pp. 12035-12038.
Sanchez-Castillo, A., et al., "On the Origin of the Optical Activity Displayed by Chiral-Ligand-Protected Metallic Nanoclusters", J. Am. Chem. Soc. 2010, vol. 132, pp. 1504-1505.
Savitha, G., et al., "Bimetallic Chiral Nanoparticles as Catalysts for Asymmetric Synthesis", Tetrahedron Letters, 2016, vol. 57, pp. 5168-5178.
Schaaff, T. Gregory, et al., "Giant Gold-Glutathione Cluster Compounds: Intense Optical Activity in Metal-Based Transitions", J. Phys. Chem. Bio., 2000, vol. 104, pp. 2630-2641.
Shemer, G., et al., "Chirality of Silver Nanoparticles Synthesized on DNA", J. Am. Chem. Soc., 2006, vol. 128, pp. 11006-11007.
Shen, C., et al., "Tuning the Structural Asymmetries of Three-Dimensional Gold Nanorod Assemblies", Chem. Commun., 2015, vol. 51, pp. 13627-13629.
Slocik, Joseph M., "Sequenced Defined Biomolecules for Nanomaterial Synthesis, Functionalization, and Assembly", Current Opinion in Biotechnology, 2017, vol. 46, pp. 7-13.
Song, Y., et al., "Enhanced Stability of Janus Nanoparticles by Covalent Cross-Linking of Surface Ligands", ACS Publications, Langmuir, 2011, vol. 27, pp. 14581-15488.
Song, Y., et al., "Janus Nanoparticles as Versatile Phase-Transfer Reagents", ACS Publications, Langmuir, 2014, vol. 30, pp. 6389-6397.
Song, Y., et al., "Janus Nanoparticles: Preparation, Characterization, and Applications", Chem. Asian J., 2014, vol. 9, pp. 418-430.
Tan, L. et al., "DNA as a Powerful Tool for Morphology Control, Spatial Positioning, and Dynamic Assembly of Nanoparticles", Acc. Chem. Res., 2014, vol. 47, pp. 1881-1890.
Tohgha, U., et al., "Ligand Induced Circular Dichroism and Circularly Polarized Luminescence in CdSe Quantum Dots", ACS Nano, 2013, vol. 7, No. 12, pp. 11094-11102.
Cecchini, Michael P. et al., "Self-Assembled Nanoparticle Arrays for Multiphase Trace Analyte Detection". Nature Materials, vol. 12, No. 2, pp. 165-171. Feb. 2013; abstract, pp. 1604, 1606-1607.
Di, Bin et al., "Anionic Surfactant Templated Chiral Nanospheres and Their Enantioselective Adsorption". New Journal of Chemistry, vol. 37, No. 5, pp. 1603-1609. 2013; abstract; pp. 1604, 1606-1607.
Isabel Martins Tiago Fernandes, Ana, "Assessment of Mixed Monolayer-Protected Gold Nanoparticies Assembly in Solution: Study and Characterization", Instituto Superior Tecnico, Universidade Technica de Lisboa, A Master's thesis, <URL: https://fenix.tecnico.ulisboa.pU downloadFile/395142041137/tese%20ana.pdf>; Sep. 2010; pp. 29, 40, 50, 67.
Song, Yang et al., "Janus Nanoparticles as Versatile Phase-Transfer Reagents", Langmuir, vol. 30, No. 22, pp. 6389-6397. Jun. 2, 2014; abstract, pp. A-D.

Xu, Li-Ping et al,. "Adhesion Force Studies of Janus Nanoparticles", Langmuir, vol. 23, No. 16, pp. 8544-8548. Jul. 31, 2007, entire document.
Zhang, Min et al., "Colorimetric Chiral Recognition of Enantiomers Using the Nucleotide-Capped Silver Nanoparticles", Analytical Chemistry, vol. 83, No. 5, pp. 1504-1509, Feb. 8, 2011; abstract; p. 1505.
Written Opinion and International Search Report dated Apr. 19, 2019 issued in corresponding PCT Appln. No. PCT/US19/17926.
Urban, Maximilian J., et al., "Plasmonic Toroidal Metamolecules Assembled by DNA Origami", J. Am. Chem. Soc., 2016, vol. 138, pp. 5495-5498.
Vidal, X., et al., "Coupled Plasmons Induce Broadband Circular Dichroism in Patternable Films of Silver Nanoparticles with Chiral Ligands", The Royal Soc. of Chemistry, Nanoscale, 2013, vol. 5, pp. 10550-10555.
Wang, Rong-Yao, et al., "Chiral Assembly of Gold Nanorods with Collective Plasmonic Circular Dichroism Response", The Royal Soc. of Chemistry, Soft Matter, 2011, vol. 7, pp. 8370-8375.
Wang, Z., et al., "Optical Chiral Metamaterials: A Review of the Fundamentals, Fabrication Methods and Applications", Nanotechnology, 2016, vol. 27, pp. 1-20.
Watanabe, K., "Helically Assembled π-Conjugated Polymers with Circularly Polarized Luminescence", Sci. Technol. Adv. Mater. , 2014, vol. 15, pp. 1-21.
Wu, X., et al., "Propeller-Like Nanorod-Upconversion Nanoparticle Assemblies with Intense Chiroptical Activity and Luminescence Enhancement in Aqueous Phase", Adv. Mater., 2016, vol. 28, pp. 5907-5915.
Xu, Q., et al., "Controlled Assembly of Janus Nanoparticles", Langmuir, 2010, vol. 26(18), pp. 14923-14928.
Xu, L., et al., "Self-Assembled Nanoparticle Dimers with Contemporarily Relevant Properties and Emerging Applications", Materials Today, 2016, vol. 19, No. 10, pp. 595-606.
Yang, Y., et al., "One-Dimensional Self-Assembly of Gold Nanoparticles for Tunable Surface Plasmon Resonance Properties", Nanotechnology, 2006, vol. 17, pp. 2821-2827.
Yasukawa, T., et al., "Chiral Ligand-Modified Metal Nanoparticles as Unique Catalysts for Asymmetric C—C Bond-Forming Reactions: How Are Active Species Generated?", ACS Catal. 2016, vol. 6, pp. 7979-7988.
Yeom, J., et al., "Chiral Templating of Self-Assembling Nanostructures by Circularly Polarized Light", Nature Materials, 2015, vol. 14, pp. 66-72.
Zhang, L., et al., "Chiral Nanoarchitectonics: Towards the Design, Self-Assembly, and Function of Nanoscale Chiral Twists and Helices", Adv. Mater., 2016, vol. 28, pp. 1044-1059.
Zhou, Y., et al., "Optical Coupling Between Chiral Biomolecules and Semiconductor Nanoparticles: Size-Dependent Circular Dichroism Absorption", Angew. Chem. Int. Ed., 2011, vol. 50, pp. 11456-11459.

\* cited by examiner

METHOD FOR DETECTION AND SEPARATION OF ENANTIOMERS USING VESICLE-LIKE NANOSTRUCTURES SELF-ASSEMBLED FROM JANUS NANOPARTICLES

CROSS REFERENCE TO RELATED APPLICATIONS

The present application is a National Stage Application under 35 U.S.C. § 371 (a) of PCT/US19/17926, filed Feb. 14, 2019, which claims the benefit of and priority to U.S. Provisional Patent Application Ser. No. 62/635,217, filed Feb. 26, 2018. The entire disclosures of all of the foregoing applications are incorporated by reference herein.

GOVERNMENT LICENSE RIGHTS

This invention was made with Government support under Grant Nos. CHE1701408 and DMR1409396, awarded by the National Science Foundation. The Government has certain rights in the invention.

BACKGROUND

Plasmonic metal nanoparticles have been found to exhibit unique chiroptical properties. Unlike conventional chiral molecules (e.g., peptides, proteins, and DNA) that typically exhibit circular dichroism ("CD") absorption in the far ultraviolet ("UV") region (140-250 nm), plasmonic circular dichroism ("PCD") in metal nanoparticles is generally observed in the visible range and can be readily manipulated by modifying the chemical nature and morphology of the nanoparticles. PCD response may be due to the formation of intrinsically chiral nanoparticle cores, capping with chiral organic ligands, as well as chiral arrangements of achiral nanoparticles into organized ensembles. Such nanoparticle ensembles may be assembled using chiral templates (e.g., DNA), which assist in the growth of nanoparticles and imprint their chirality onto the nanoparticle core during the growth process, resulting in the formation of chiral nanoparticles.

For achiral plasmonic nanoparticles, PCD may also be produced by using chiral capping ligands, which results in strong dipole and higher-order interactions between the ligands' and nanoparticle core's electrons responsible for PCD. Upon interactions with the chiral ligands, the symmetry of the electronic property on the nanoparticle surface is distorted, leading to different extinction coefficients between the left-handed and right-handed circularly polarized light. These properties of plasmonic nanoparticles may be leveraged to detect and separate enantiomers of analytes due to inherent chiroptical properties.

SUMMARY

The present disclosure provides a method for detecting and separating enantiomers of an analyte. The method includes adding a plurality of amphiphilic nanoparticles to a solvent to form a plurality of hollow, enantioselective nanoparticle ensembles. The amphiphilic nanoparticles may be Janus nanoparticles. As used herein, a Janus nanoparticle is a nanoparticle whose surface incudes two different chemical and/or physical properties. In embodiments, the Janus nanoparticles may include a metallic core having a first surface portion and a second surface portion. The first portion includes hydrophobic ligands, while the second portion includes hydrophilic ligands, such that when the Janus nanoparticles are added to a solvent, the nanoparticles self-assemble into larger, hollow nanoparticle ensembles.

The method further includes obtaining a circular dichroism ("CD") spectrum (first spectrum) of the mixture of the nanoparticle ensembles. Thereafter, an analyte is added to the mixture and a CD spectrum of the mixture (second spectrum) is obtained. The nanoparticle ensembles bind to one of the enantiomers of the analyte, if any enantiomers are present, and the spectra are analyzed by determining a difference between one or more points (e.g., peaks) which is indicative of whether the analyte includes any enantiomers.

The present disclosure also provides a method for separating enantiomers of an analyte. The method includes adding a plurality of amphiphilic nanoparticles to a solvent to form a plurality of hollow, enantioselective nanoparticle ensembles as described above. The nanoparticle ensembles are then added to an analyte having D and L enantiomers such that the nanoparticle ensembles bind to one of the enantiomers. The nanoparticle ensembles along with enantiomers that are bound to the ensembles are separated from the mixture, leaving the counterpart enantiomers in the mixture.

According to one embodiment of the present disclosure, a method for processing an analyte is disclosed. The method includes: adding a plurality of amphiphilic nanoparticles to a solvent to form a mixture having a plurality of enantioselective nanoparticle ensembles; adding an analyte to the mixture to form an analyte mixture; obtaining a test circular dichroism spectrum of the analyte mixture; and determining an enantiomeric property of the analyte based on a comparison of a baseline circular dichroism spectrum of the analyte mixture to the test circular dichroism spectrum.

According to one aspect of the above embodiment, the method further includes: forming the plurality of amphiphilic nanoparticles, each of the plurality of amphiphilic nanoparticles includes a metallic core having a first surface portion and a second surface portion, the first surface portion including hydrophobic ligands and the second surface portion including hydrophilic ligands.

According to another aspect of the above embodiment, forming the plurality of amphiphilic nanoparticles includes: contacting a plurality of precursor nanoparticles each of which includes the metallic core with the hydrophobic ligands; and replacing a portion of the hydrophobic ligands with the hydrophilic ligands in a ligand-exchange reaction, which may include forming a monolayer of the precursor nanoparticles on a surface of a water subphase and adding the hydrophilic ligands to the subphase.

According to a further aspect of the above embodiment, the plurality of amphiphilic nanoparticles is added to a polar solvent, which may be selected from the group consisting of water, tetrahydrofuran, chloroform, and dichloromethane.

According to one aspect of the above embodiment, adding the analyte to the mixture includes binding a nanoparticle ensemble of the plurality of enantioselective nanoparticle ensembles to a molecule of the analyte.

According to another aspect of the above embodiment, the method also includes separating L-form enantiomers of the analyte from D-form enantiomers of the analyte. Separation of L-form enantiomers of the analyte from D-form enantiomers of the analyte includes binding the L-form enantiomers or the D-form enantiomers with the plurality of enantioselective nanoparticle ensembles and subsequently, removing the plurality of enantioselective nanoparticle ensembles bound to the L-form enantiomers or the D-form enantiomers from the mixture.

According to another aspect of the above embodiment, adding the plurality of amphiphilic nanoparticles to the solvent forms a plurality of hollow enantioselective nanoparticle ensembles without assistance of a template or a scaffold.

According to another embodiment of the present disclosure, a kit for processing an analyte is disclosed. The kit includes: a first reagent having a plurality of amphiphilic nanoparticles, each of the plurality of amphiphilic nanoparticles including a metallic core having a first surface portion and a second surface portion, the first surface portion including hydrophobic ligands and the second surface portion including hydrophilic ligands; and a second reagent including a polar solvent, wherein adding the first reagent to the second reagent forms a mixture having a plurality of nanoparticle ensembles.

According to one aspect of the above embodiment, the metallic core includes gold, the hydrophobic ligands include 1-hexanethiolate, and the hydrophilic ligands include 3-mercapto-1,2-propanediol.

According to another aspect of the above embodiment, the nanoparticle ensembles have an average lateral dimension from about 50 nanometers to about 200 nanometers.

According to another aspect of the above embodiment, the kit further includes a baseline circular dichroism spectrum of the mixture having the plurality of nanoparticle ensembles. The kit further includes a third reagent container including a second solvent for forming an analyte solution with an analyte. The kit also includes instructions for: mixing at least a portion of the mixture having the plurality of nanoparticle ensembles with the analyte solution; obtaining a test circular dichroism spectrum of the mixture with the analyte solution; and determining an enantiomeric property of the analyte based on a comparison of a baseline circular dichroism spectrum of the mixture to the test circular dichroism spectrum.

BRIEF DESCRIPTION OF DRAWINGS

Various embodiments of the present disclosure will be described herein below with reference to the figures wherein.

DETAILED DESCRIPTION

The present disclosure is directed to amphiphilic Janus nanoparticles that self-assemble into micelle-like, hollow nanoparticle ensembles, without the aid of any chiral templates or scaffolds when placed in a polar solvent. While the Janus nanoparticles according to the present disclosure are not chiral, the hollow nanoparticle ensembles are, which allows them to selectively bind to optical enantiomers of analytes. The present disclosure provides a method of using the nanoparticle ensembles for detection and/or separation of enantiomers due to their chiroptical properties of nanoparticle ensembles.

The Janus nanoparticles according to the present disclosure include a metallic core which may be formed from any suitable metal. The metallic core includes a first surface portion having hydrophobic ligands and a second surface portion having hydrophilic ligands, thus, making the Janus nanoparticle amphiphilic.

The metallic core may be a metallic nanoparticle having an average diameter of from about 1 nm to about 10 nm, in embodiments from about 2 nm to about 6 nm. In embodiments, the metallic core may include any metal, such as gold (Au), platinum (Pt), silver (Ag), palladium (Pd), copper (Cu), ruthenium (Ru), iridium, (Ir), rhodium (Rh), or combinations thereof. Gold nanoparticles may be synthesized using the Brust method, which involves dissolving hydrogen tetrachloroauric salt in a non-aqueous solvent, such as toluene, and using tetraoctylammonium bromide as a phase-transfer catalyst and sodium borohydride to reduce gold(III) to gold(0). An exemplary synthesis of gold nanoparticles that are suitable as metallic cores is disclosed in Example 1.

The metallic nanoparticles are then be used to attach first, e.g., hydrophobic, ligands and second, e.g., hydrophilic, ligands to form two surface portions. Suitable hydrophobic ligands include, but are not limited to, alkanethiols such as 1-hexanethiol, 1-octanethiol, 1-decanethiol, etc. Suitable hydrophilic ligands include, but are not limited to, hydroxyterminated thiols, such as 3-mercapto-1,2-propanediol, and 2-(2-mercaptoethoxy)ethanol.

Initially, the first ligands are attached to the surface of the metallic nanoparticles. After the metallic nanoparticles have been capped by the first ligands a portion of the capped ligands are replaced by the second ligands to form Janus nanoparticles according to the present disclosure. In embodiments, the second ligands may be capped through an interfacial ligand exchange reaction using a Langmuir-Blodgett trough.

Figure 4:
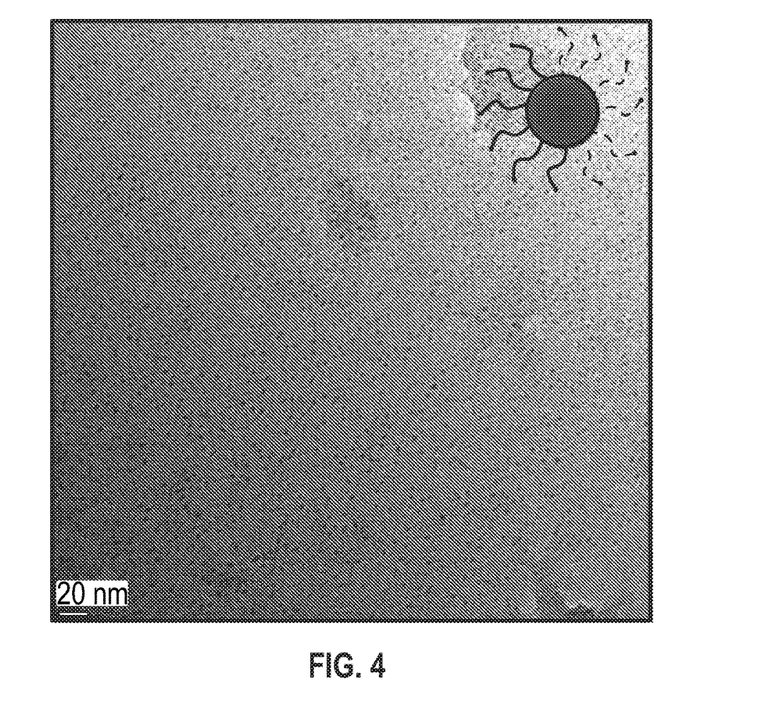
FIG. 4 is a transmission electron microscope image of gold Janus nanoparticles according to an embodiment of the present disclosure.

A schematic representation of the Janus nanoparticles formed using interfacial ligand exchange reaction is shown in an upper right corner of FIG. 4, in which a circle represents a metallic core, solid lines extending from the metallic core represent hydrophobic ligands and dashed lines extending from the metallic core represent hydrophilic ligands. As shown in FIG. 4, the Janus nanoparticles includes the hydrophilic ligands disposed on one portion of the surface of the metallic core and the hydrophobic ligands disposed on another portion of the surface of the metallic core.

Figure 6:
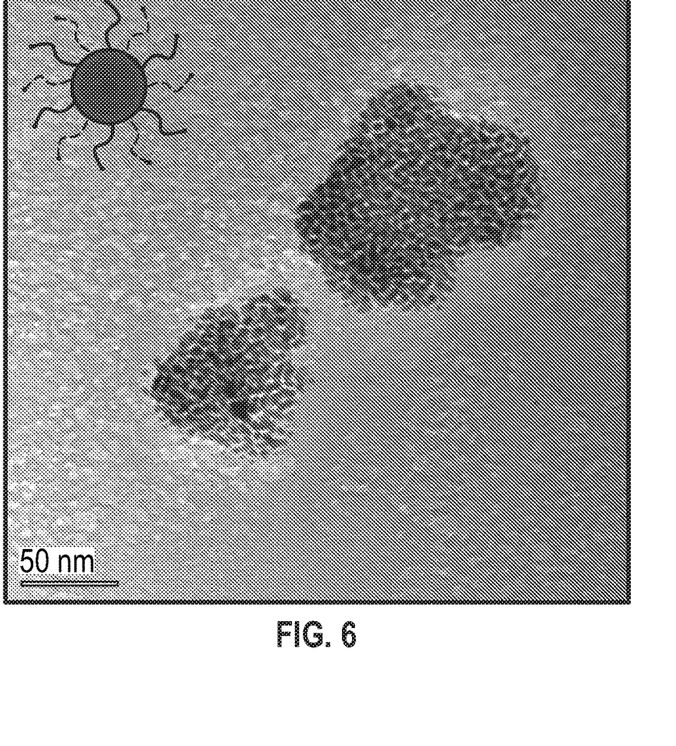
FIG. 6 is a transmission electron microscope image of solid ensembles of gold bulk-exchange nanoparticle according to an embodiment of the present disclosure.

In further embodiments, the second ligands may be capped through a bulk ligand exchange reaction. Exemplary syntheses of Janus nanoparticles, including the interfacial ligand exchange reaction and the bulk exchange reaction, are disclosed in Example 3. A schematic representation of the nanoparticles formed using the bulk ligand exchange reaction is shown in an upper left portion of FIG. 6, in which a circle represents a metallic core, the solid lines extending from the metallic core represent hydrophobic ligands and the dashed lines extending from the metallic core represent hydrophilic ligands. As shown in FIG. 6, the hydrophilic ligands and the hydrophobic ligands are interspersed with one another on the surface of the metallic core rather than being separated on two separate surface portions as shown in FIG. 4.

The ligand exchange reaction may be carried out from about 1 hour to about 10 hours. The length of the reaction affects the surface concentration of the second ligand. In particular, the longer the time of the ligand exchange reaction, the larger the amount of the second ligand. In embodiments, the ligand exchange reaction may be carried out until surface concentration of the second ligand is from about 15% to about 70% of the total ligands of the Janus nanoparticles.

Once the Janus nanoparticles are formed, the Janus nanoparticles may be used to form nanoparticle ensembles. This may be accomplished by adding the Janus nanoparticles to a polar solvent, which include, but are not limited to, water, tetrahydrofuran, chloroform, dichloromethane, dimethylformamide. The Janus nanoparticles behave similarly to amphiphilic surfactant molecules and self-assemble into hollow, micelle-like nanoparticle ensembles. The Janus nanoparticles self-assemble once the concentration in the polar solvent is at or above a critical micelle concentration ("CMC"). In embodiments, CMC may be from about 0.05 milligrams per milliliter ("mg/mL") to about 0.2 mg/mL. The Janus nanoparticle ensembles may have an average nanoparticle size from about 50 nanometers ("nm") to about 200 nm.

Figure 5:
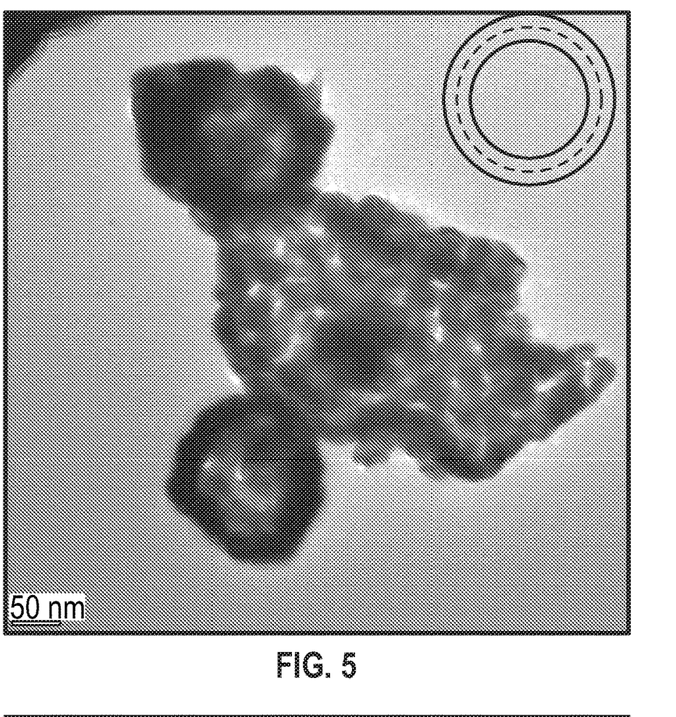
FIG. 5 is a transmission electron microscope image of a hollow gold Janus nanoparticle ensemble according to an embodiment of the present disclosure.

A schematic representation of a cross section of the Janus nanoparticle ensemble is shown in an upper right corner of FIG. 5. The Janus nanoparticle ensemble includes a bilayer shell having an inner layer shown as an inner solid circle, a middle layer shown as a dashed circle, and an outer layer shown as an outer solid circle. The Janus nanoparticle ensemble also defines an inner volume within the bilayer enclosing the solvent. The inner and outer layers are formed from hydrophilic surfaces of the Janus nanoparticles in the presence of a polar solvent, with the middle layer being formed from the hydrophobic surfaces of the Janus nanoparticles due to self-assembly and orientation of the Janus nanoparticles.

The Janus nanoparticle ensembles according to the present disclosure are PCD active, as detailed in Example 4 below. This property allows the Janus nanoparticle ensembles to be used as nanoscale vehicles for enantioselective phase transfer of chiral molecules of analytes, leading to separation and detection of optical isomers of analytes.

Separation and identification of optical isomers may be accomplished by forming Janus nanoparticle ensembles and then adding the same to the analyte. Janus nanoparticles may be added to any suitable solvent at a concentration that is at or above CMC to allow the Janus nanoparticles to self-assemble into nanoparticle ensembles. A solution of the analyte is also formed using any suitable solvent. Amount of analyte dissolved in the solutions may be from about 80 to about 120 times the amount of surface ligands of the nanoparticle ensembles to ensure that all of nanoparticle ensembles are fully saturated by the analyte.

A CD spectrum of the Janus nanoparticles is used as baseline spectrum. The nanoparticle ensembles are then mixed with the analyte solution. After the nanoparticle ensembles are mixed with the analyte solution, a combined CD spectrum of the resulting mixture is obtained. The combined CD spectrum is compared to the baseline spectrum. In embodiments, the analysis of the CD spectra may be performed manually by a technician or automatically by a computing device having access to the CD spectra. The analysis of the spectra may include determining differences between specific absorption peaks of individual spectra, e.g., difference between specific points at specific wavelengths of the spectra in millidegrees ("mdeg"). Thus, a difference between the baseline and combined CD spectra is above a predetermined threshold is indicative that the nanoparticle ensembles bound with the analyte and in particular that the analyte includes enantiomers that have bound with the nanoparticle ensembles. The threshold difference between the baseline and combined CD spectra that is indicative of the nanoparticle ensembles binding to enantiomers of the analytes may be from about 5 mdeg to about 30 mdeg.

In addition to being used to detect the presence of enantiomers, the Janus nanoparticles may also be used to separate D and L enantiomers of analytes. Separation of enantiomers may be carried out in a similar manner as detection in that initially the Janus nanoparticles are mixed with the solvent to form the nanoparticle ensembles. Once formed, the nanoparticle ensembles may be added to a racemic mixture of an analyte. At this point, the nanoparticle ensembles bind to one of the enantiomers of the analyte. Thereafter, the bound nanoparticle ensembles may be removed from the mixture with the analyte. The bound nanoparticle ensembles may be removed via filtration or any other suitable techniques, such as centrifugation, and dialysis. After the bound nanoparticle ensembles are removed, the non-bound enantiomer remains in the mixture, thereby separating the enantiomers of the analyte.

The present disclosure also provides a kit for detecting and/or separating enantiomers. The kit includes a first reagent container having the Janus nanoparticles and a second reagent container having the polar solvent. The first container may include from about 15 mg to about 150 mg of the Janus nanoparticles and the second container may include from about 100 mL to about 1,000 mL of the solvent. The kit may also include instructions providing directions for using the kit including the amounts at which the Janus nanoparticles should be mixed with the solvent to prepare a nanoparticle mixture having a desired concentration of the Janus nanoparticles such that nanoparticle ensembles are formed. The concentration of the Janus nanoparticles may be from about 0.05 mg/mL to about 0.20 mg/mL. The amounts of the Janus nanoparticles in the first container and the solvent in the second container may be premeasured such that the contents of the two containers may be combined to achieve the desired concentration. In further embodiments, the kit may include a single reagent container that includes a nanoparticle mixture having the plurality of nanoparticle ensembles dispersed in the solvent.

The kit may also include instructions for preparing an analyte solution. In embodiments, the kit may include a third container including a solvent for dissolving the analyte. The instructions may list the concentration for the analyte solution, which may be from about 5 millimolar to about 150 millimolar. In addition, the instructions may also list the amounts at which the nanoparticle mixture and the analyte solution should be mixed such that the amount of analyte is from about 80 to about 120 times the amount of surface ligands of the nanoparticle ensembles of the nanoparticle mixture to ensure that all of nanoparticle ensembles are fully saturated by the analyte.

The instructions may also provide directions for mixing the nanoparticle ensembles and the analyte solution as well as directions for obtaining the baseline spectrum or a previously taken baseline spectrum of the nanoparticle ensembles mixture. The instructions may also provide directions for obtaining the combined spectrum of the mixture of the nanoparticle ensembles and the analyte. Further, the kit may include instructions on how to analyze the CD spectra in a manner described above to determine whether the nanoparticle ensembles have been bound to enantiomers, if any, of the analyte. With respect to separation of enantiomers of the analyte, the kit may also include instructions on how to remove enantiomers that are bound to the nanoparticle ensembles from the mixture in a manner described above.

The following Examples illustrate embodiments of the present disclosure. These Examples are intended to be illustrative only and are not intended to limit the scope of the present disclosure. Also, parts and percentages are by weight unless otherwise indicated. As used herein, "room temperature" or "ambient temperature" refers to a temperature from about 20° C. to about 25° C.

EXAMPLES

Example 1

Figure 1:
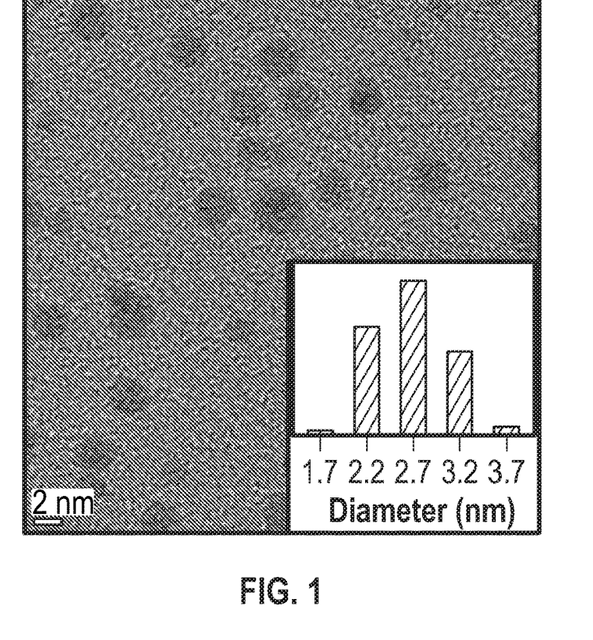
FIG. 1 is a transmission electron microscope image of gold nanoparticles having 1-hexanethiol ligands according to an embodiment of the present disclosure.

This example describes preparation of gold ("Au") nanoparticles having 1-hexanethiol ("C6SH") ligands bound thereto. Gold nanoparticles were synthesized by mixing about 30 milliliters ("mL") of an aqueous solution of hydrogen tetrachloroauric trihydrate salt ($HAuCl_4 \cdot 3H_2O$) having a concentration of about 0.03 moles per liter ("M") with about 20 mL of a solution of tetra-n-octylammonium bromide ("TOABr") in toluene having a concentration of about 0.2 M. The organic phase of the mixture was orange in color and was collected after separation. About 150 microliters ("µL") or about 1.05 millimoles ("mmol") of C6SH was injected with a micropipette into the organic phase under magnetic stirring, at which point the solution became colorless. About 24 mL of a chilled aqueous solution of sodium borohydride ("$NaBH_4$") having a concentration of about 0.43 M into the reaction mixture turning it a dark brown color, which indicated the formation of gold nanoparticles. The reaction mixture was stirred for about 4 hours, after which the organic phase was collected, dried by rotary evaporation, and washed five times with methanol to remove excess C6SH, phase-transfer catalysts, and reaction byproducts. The resulting AuC6 nanoparticles were imaged using a Philips CM300 transmission electron microscope operated at about 300 kV and had an average core diameter of 2.7±0.4 nanometers ("nm") as shown in FIG. 1.

Example 2

This example describes preparation of gold nanoparticles having 3-mercapto-1,2-propanediol ("MPD") ligands bound thereto. AuMPD microspheres were prepared using a similar process as described in Example 1 except about 1.05 millimoles of MPD were added to the organic phase instead of C6SH.

Example 3

This example describes preparation of AuC6-MPD Janus nanoparticles. About 1.5 mg ($8.42 \times 10^{-6}$ mmol) of AuC6 nanoparticles of Example 1 were dispersed in toluene and the mixture was deposited onto a water surface of a NIMA 611D Langmuir-Blodgett trough available from Biolin Scientific. Toluene was evaporated forming a nanoparticle monolayer, which was then compressed to a desired surface pressure such that the interparticle spacing was less than twice the fully extended chain length of the C6SH ligands of the AuC6 nanoparticles.

About 68.6 mg (0.634 mmol) of MPD were injected into the water subphase of the Langmuir-Blodgett trough using a micropipette to initiate an interfacial ligand exchange reaction. The resulting Janus nanoparticles were collected at about 1 hour, 4 hours, and 10 hours (hereinafter "JNP1," "JNP4," and "JNP10," respectively) so as to vary the concentration of the MPD ligands disposed on the nanoparticle surface. The collected nanoparticles were removed from the water and surface washed with methanol.

As a control, about 15 mg ($8.42 \times 10^{-5}$ mmol) of AuC6 nanoparticles of Example 1 were also mixed with MPD in tetrahydrofuran ("THF") for about 10 hours to carry out a ligand exchange reaction. The resulting bulk exchange ("BE") nanoparticles were collected and washed with methanol.

Figure 2:
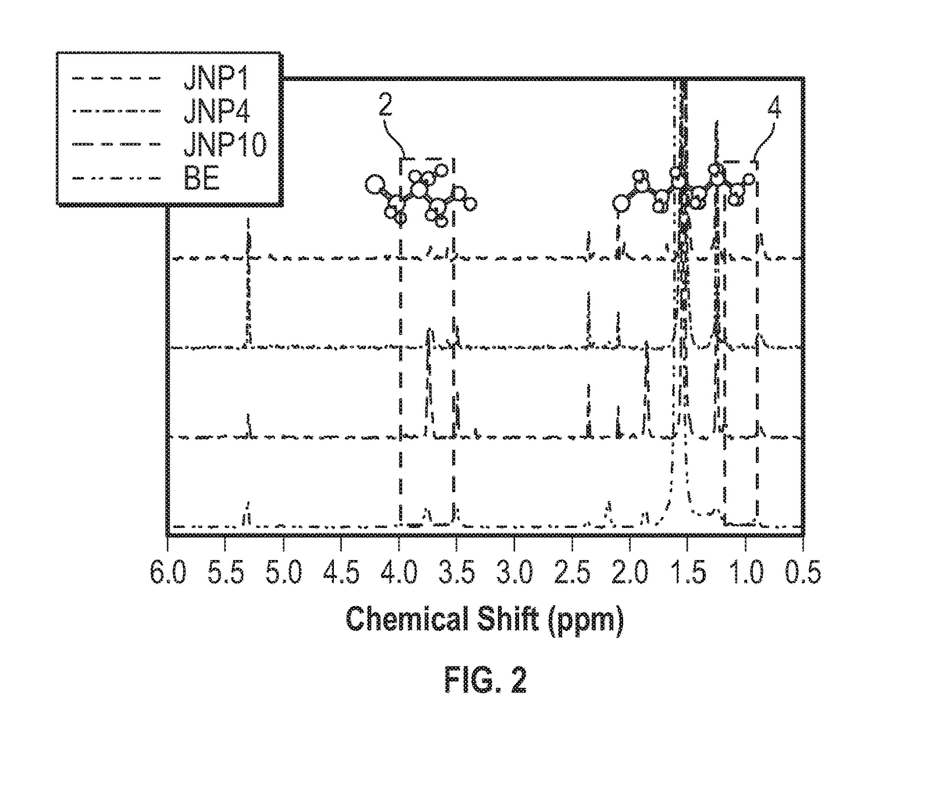
FIG. 2 is a plot of proton nuclear magnetic resonance spectra of gold Janus nanoparticles according to an embodiment of the present disclosure.

Proton nuclear magnetic resonance ("$^1$H NMR") spectra of JNP1, JNP4, JNP10, and BE nanoparticles were obtained using a Varian Unity 500 MHz spectrometer with the samples dissolved in deuterated chloroform ($CDCl_3$) and are shown in FIG. 2. Based on the ratio of the integrated peak areas of the terminal $CH_3$ protons of the MPD ligands and CHOH—$CH_2$OH protons of the C6SH ligands as shown in regions 2 and 4, respectively, the MPD surface coverage was estimated to be about 17.5% for JNP1, about 28.3% for JNP4, about 61.4% for JNP10, and about 66.0% for BE nanoparticles.

Figure 3:
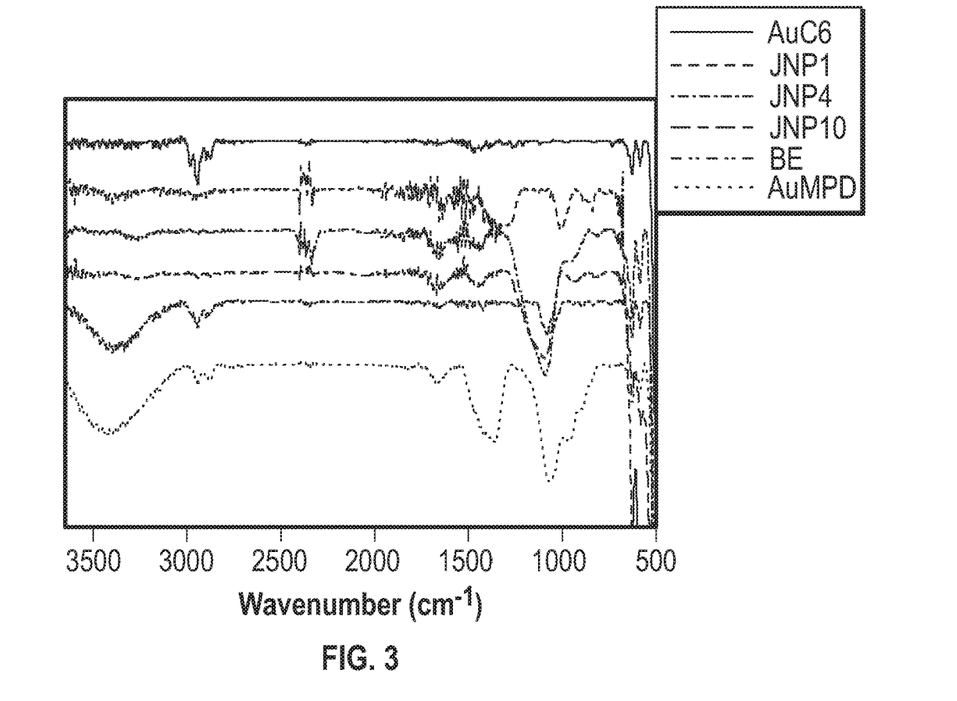
FIG. 3 is a plot of Fourier-transform infrared ("FTIR") spectra of gold Janus nanoparticles according to an embodiment of the present disclosure.

Fourier-transform infrared ("FTIR") spectra of AuC6, JNP1, JNP4, JNP10, BE, and AuMPD nanoparticles were obtained using a PerkinElmer Spectrum One spectrometer and are shown in FIG. 3. JNP10 and BE nanoparticles appeared to behave as structural isomers with a similar core-ligand composition but a different surface distribution of the capping ligands. The incorporation of MPD ligands onto the nanoparticle surfaces was manifested in FTIR measurements, where the O—H stretch was found at about 3300-3200 $cm^{-1}$ and the C—O vibration at about 1030 $cm^{-1}$.

Example 4

This example describes formation of JNP10 and BE nanoparticle ensembles in a polar solvent. JNP10 nanoparticles were dispersed in water at a concentration of about 0.01 mg/mL. As shown in FIG. 4, which is a transmission electron microscope ("TEM") image of the first JNP10 nanoparticle aqueous mixture, the JNP10 nanoparticles were well dispersed in water as individual nanoparticles without apparent agglomeration.

A second aqueous mixture having a concentration of about 0.15 mg/mL of JNP10 nanoparticles was also prepared. It was observed that JNP10 nanoparticles behaved similarly to amphiphilic surfactant molecules, such as octyl phenol ethoxylate, and self-assembled into organized ensembles. As shown in FIG. 5, which is a TEM image of the second JNP10 nanoparticle aqueous mixture, the nanoparticles formed micelle-like, hollow organized ensembles with lateral dimensions from about 50 nm to about 200 nm.

A third aqueous mixture of BE nanoparticles was also prepared. As shown in FIG. 6, which is a TEM image of the BE nanoparticle mixture, BE nanoparticles also formed nanoparticle ensembles of similar dimensions to the ensembles formed by JNP10 nanoparticles. However, unlike the ensembles formed by JNP10 nanoparticles, which were hollow, the BE nanoparticle ensembles were solid.

Formation of the hollow ensembles by the JNP10 nanoparticles is caused by the segregated distribution of the hydrophobic C6SH ligands and the hydrophilic MPD ligands on the surface of the JNP10 nanoparticles as shown in FIG. 4. This distribution allows for the JNP10 nanoparticles to arrange themselves into micelle-like structures as shown in FIG. 5. Conversely, the BE nanoparticles, which include a random mix of C6SH and MPD ligands make it difficult for the BE nanoparticles to orient themselves with minimal surface energy to make it conducive to form similar ensembles as shown in FIG. 6.

Figure 7A:
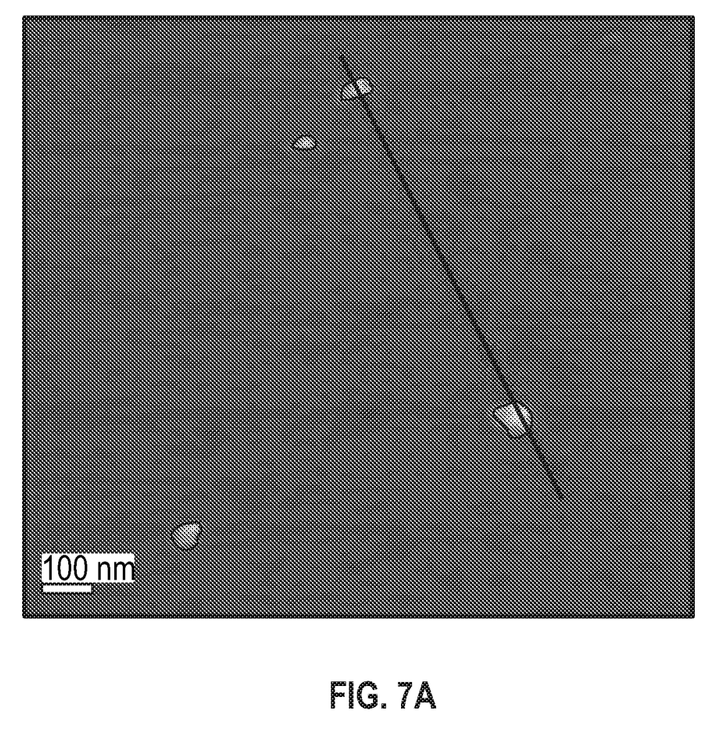
FIG. 7A is an atomic force microscope image of gold Janus nanoparticle ensembles in water at a first concentration according to an embodiment of the present disclosure.
Figure 7B:
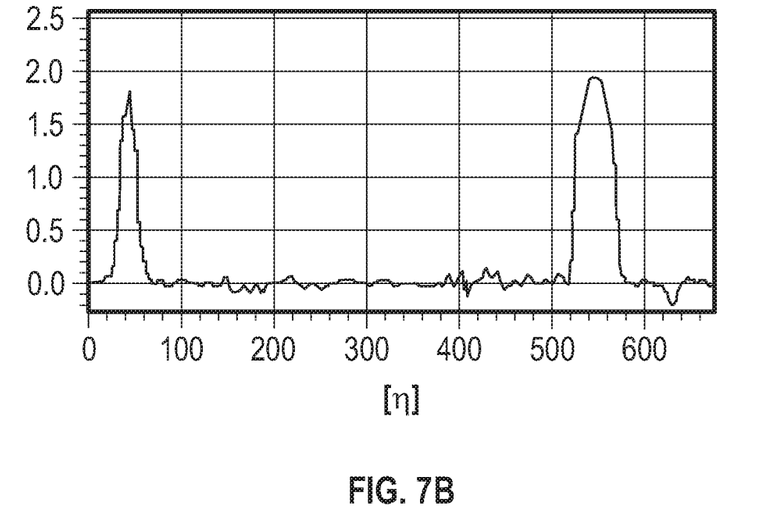
FIG. 7B is a plot of a height profile of a line scan drawn through the gold Janus nanoparticle ensembles of FIG. 7A.
Figure 8A:
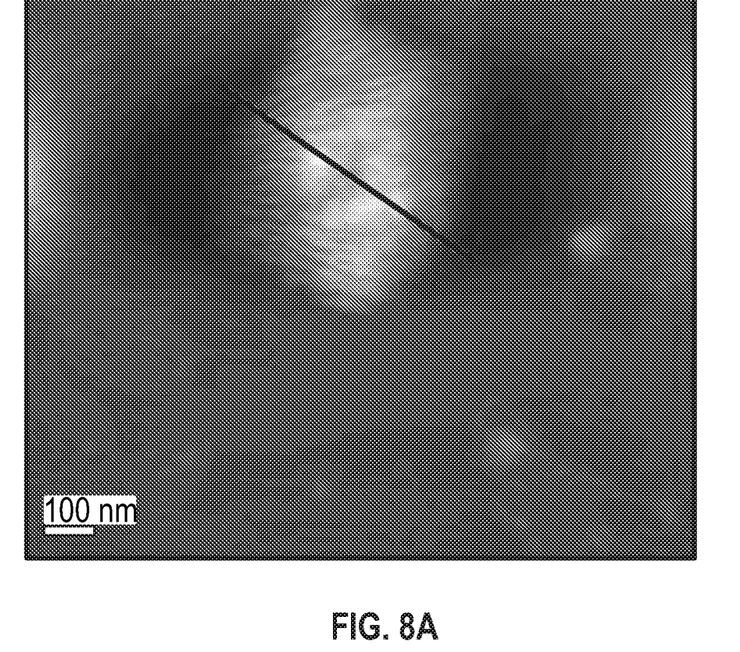
FIG. 8A is an atomic force microscope image of gold Janus nanoparticle ensembles in water at a second concentration higher than the first concentration according to an embodiment of the present disclosure.
Figure 8B:
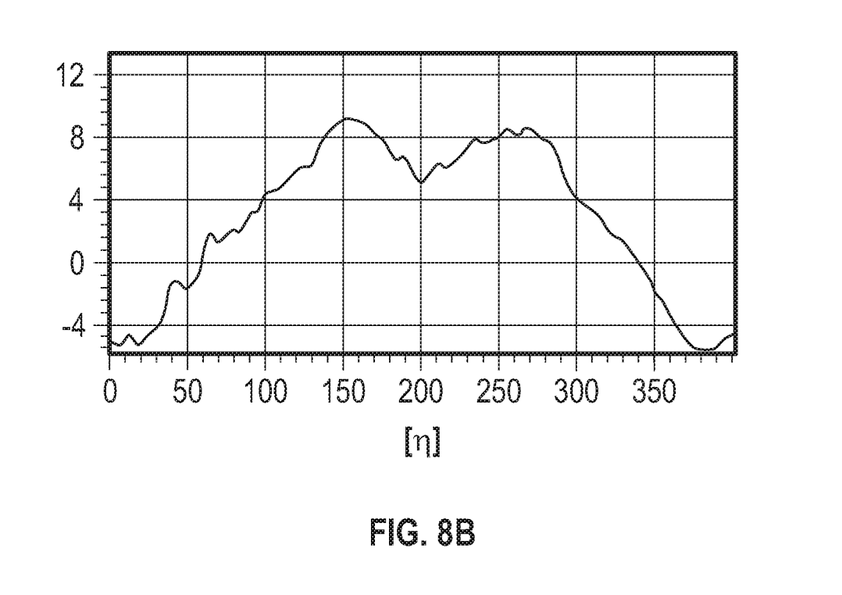
FIG. 8B is a plot of a height profile of a line scan drawn through the gold Janus nanoparticle ensembles of FIG. 8A.

Atomic force microscopic ("AFM") studies were performed on JNP10 nanoparticles using a Molecular Imaging PicoLE SPM instrument to confirm formation of ensembles of JNP10 nanoparticles. The image of the first JNP10 aqueous mixture is shown in FIG. 7A and the image of the second JNP10 aqueous mixture is shown in FIG. 8A. In particular, FIG. 7A shows the lack of larger nanoparticle assemblies, which were present in FIG. 8A. The corresponding plots of FIGS. 7B and 8B illustrate height profiles of the line scans in the corresponding images.

Figure 9:
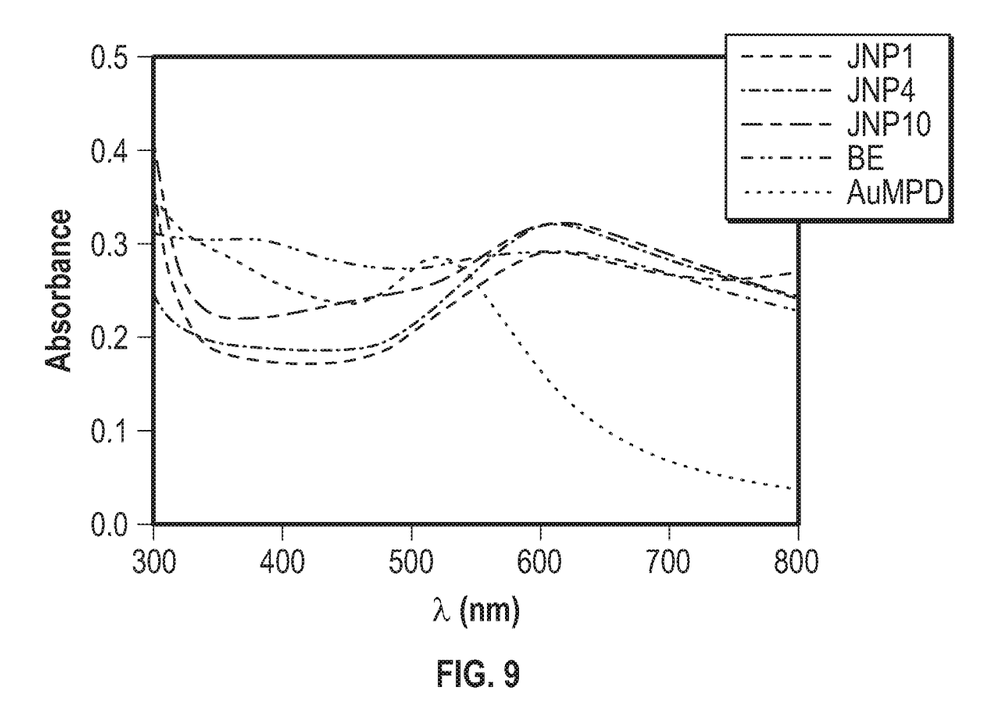
FIG. 9 is a plot of ultraviolet-visible absorbance spectra of various gold nanoparticles according to an embodiment of the present disclosure.
Figure 10:
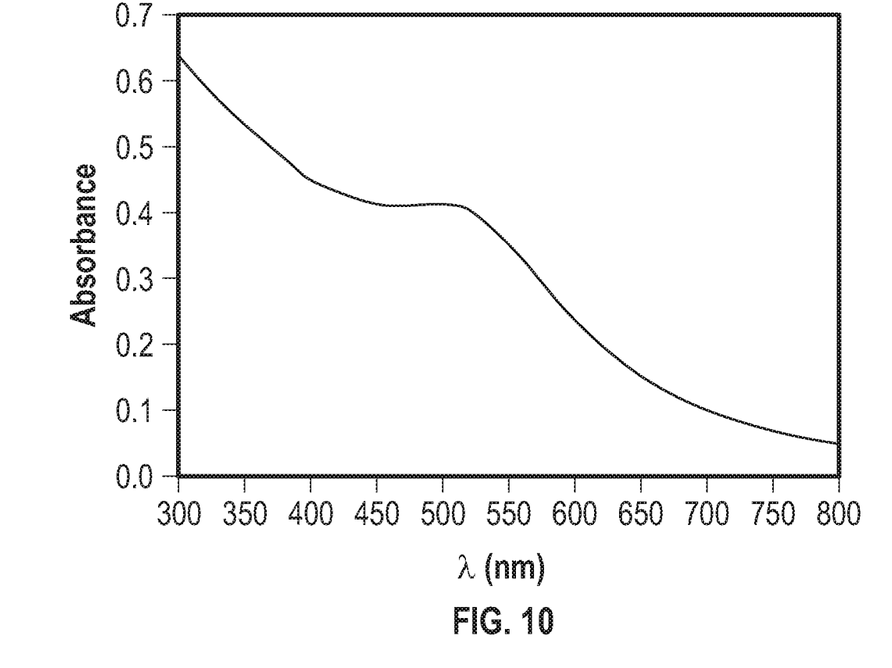
FIG. 10 is a plot of ultraviolet-visible absorbance spectrum of gold nanoparticles having -1-hexanethiol ligands.

Optical properties of the JNP1, JNP4, JNP10, BE, and AuMPD nanoparticles in water at a concentration of about 0.15 mg/mL and of the AuC6 nanoparticles in chloroform ("CHCl$_3$") were studied using a PerkinElmer Lambda 35 UV-Vis Spectrometer with a 1 centimeter ("cm") quartz cuvette. With reference to FIG. 9, UV-vis absorption spectra of the JNP1, JNP4, JNP10, BE, and AuMPD nanoparticles in water are shown. Similarly, FIG. 10 shows a UV-vis absorption spectra of AuC6 nanoparticles in CHCl$_3$. The spectra of the JNP1, JNP4, JNP10, and BE nanoparticles (FIG. 9) showed a broad absorption peak at about 610 nm and a marked red-shift of about 100 nm unlike the spectrum of AuC6 nanoparticles (FIG. 10) and AuMPD nanoparticles (FIG. 9). The difference between the spectra of JNP1, JNP4, JNP10, and BE nanoparticles and AuMPD and AuC6 nanoparticles are due to strong interparticle electronic interactions as a result of the formation of nanoparticle ensembles of the Janus nanoparticles.

Figure 11:
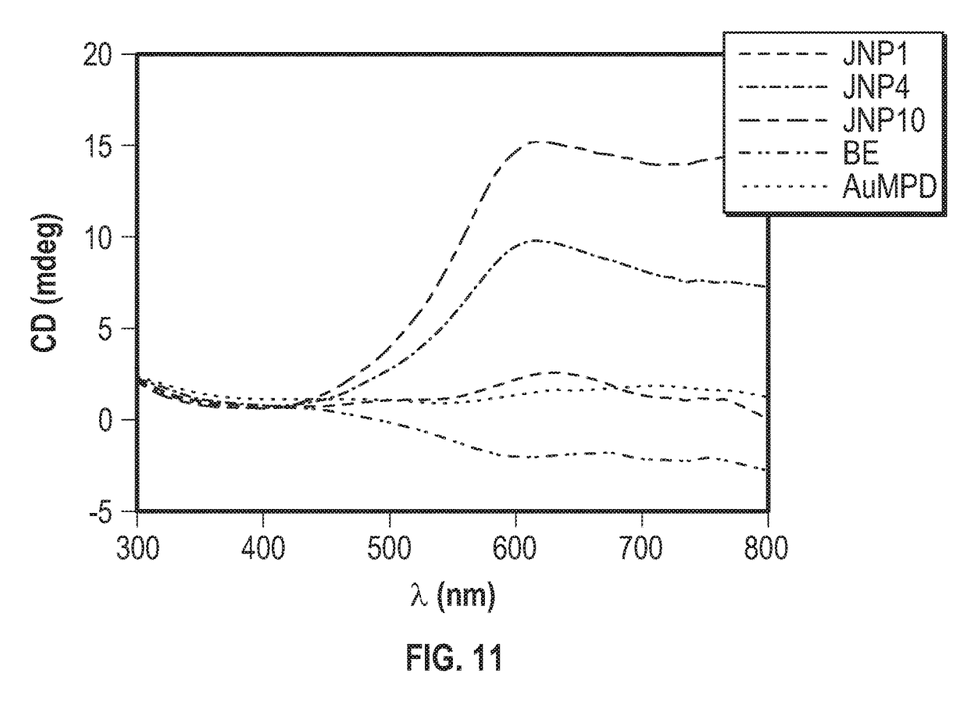
FIG. 11 is a plot of circular dichroism spectra of various gold nanoparticles according to an embodiment of the present disclosure.

CD spectra of JNP1, JNP4, JNP10, BE, and AuMPD nanoparticles were also studied. Each of the samples was placed in a 1 centimeter quartz cuvette which was then subjected to circular dichroism measurements using a JASCO J1500 CD spectrometer. With reference to FIG. 11, which shows CD spectra of JNP1, JNP4, JNP10, BE, and AuMPD nanoparticles, it was observed that the JNP1, JNP4, and JNP10 nanoparticle ensembles exhibited PCD signals at wavelength greater than 500 nm, with the intensity maxima matching the corresponding peaks of the absorbance spectra of FIG. 9.

The PCD intensity increased with increasing MPD concentration on the nanoparticle surface, namely, about +2.6 millidegree ("mdeg") for JNP1 nanoparticles, about +9.9 mdeg for JNP4 nanoparticles, and about +15.2 mdeg for JNP10 nanoparticles. This indicates that increasing dissymmetry of the distribution of surface capping ligands, namely, MPD, facilitates the formation of micelle-like, hollow nanoparticle ensembles that are PCD-active. In contrast, BE nanoparticles, exhibited only a weak PCD signal, namely, about −2.05 mdeg, despite a ligand composition and absorption similar to that of JNP10. This is due to the fact that the solid ensembles of the BE nanoparticles were PCD-inactive. In addition, AuMPD nanoparticles exhibited virtually no PCD signals, which suggest that the MPD ligands, which are racemic, provide only a limited contribution to the PCD signals of the JNP1, JNP4, and JNP10 nanoparticles, which are themselves optically chiral. Accordingly, the PCD signals of the JNP1, JNP4, and JNP10 nanoparticles are due to the structure of the ensembles themselves rather than the constituent ligands.

It was also observed that the PCD intensity of JNP1, JNP4, and JNP10 samples varied with nanoparticle concentration. As noted above, formation of nanoparticle ensembles occurred when the nanoparticle concentration reached critical micelle concentration, which was estimated to be about 0.05 mg/mL based on the variation of the PCD intensities of JNP10 nanoparticles.

Figure 12:
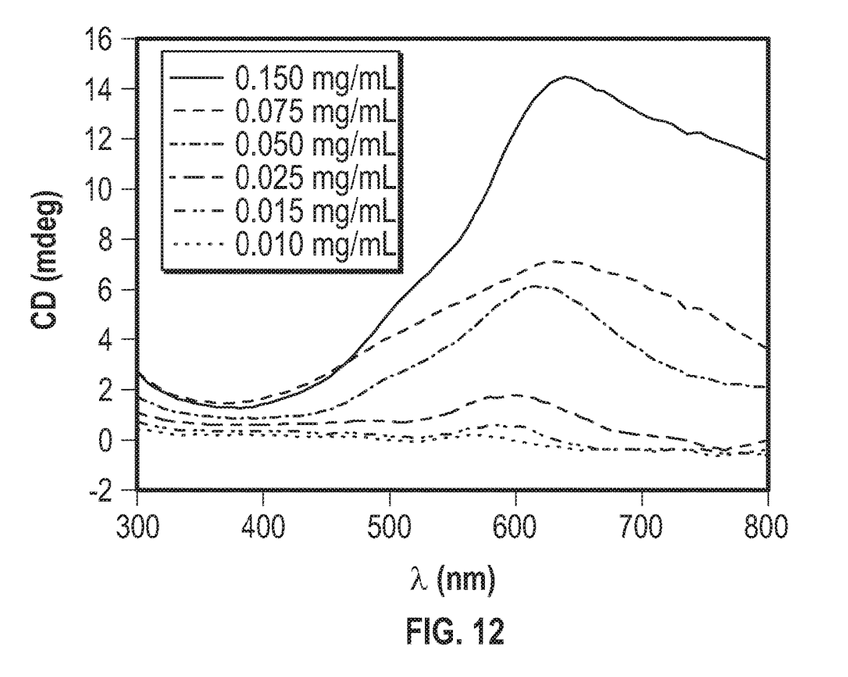
FIG. 12 is a plot of circular dichroism spectra of gold Janus nanoparticle ensembles at varying concentrations in water according to an embodiment of the present disclosure.

With reference to FIG. 12, the spectra of JNP10 nanoparticles at varied concentrations in water is shown, namely, at 0.150 mg/mL, 0.075 mg/mL, 0.050 mg/mL, 0.025 mg/mL, 0.015 mg/mL, and 0.010 mg/mL. At 0.025 mg/mL, 0.015 mg/mL, and 0.010 mg/mL concentrations, the JNP10 nanoparticles exhibited virtually no PCD absorptions, due to low dilution of the nanoparticles preventing formation of nanoparticle ensembles and the JNP10 nanoparticles themselves being PCD-inactive. However, at concentrations 0.050 mg/mL and above, JNP10 nanoparticles exhibited PCD signals with increased intensity corresponding to increased concentration, indicating that the nanoparticle concentration was sufficiently high for the formation of optically chiral nanoparticle ensembles. In particular, JNP10 nanoparticles at the higher concentrations showed broad PCD absorption peaks at about 610 nm of +6.1 mdeg for the 0.05 mg/mL solution, +7.1 mdeg for the 0.075 mg/mL solution, and +15.2 mdeg for the 0.15 mg/mL solution. The PCD intensity observed for the JNP10 ensembles was about 20 times stronger than for simple nanoparticle dimers, trimers, tetramers, and helical structures that have been previously reported in the prior art. This further confirms that the PCD effects were primarily due to the formation of micelle-like nanoparticle ensembles by self-assembly of JNP10 nanoparticles.

Example 5

This example describes detection and separation of D,L-alanine using JNP10 nanoparticles. Chirality of the hollow micelle-like JNP10 nanoparticle ensembles of Example 4 allows for using these ensembles as nanoscale vehicles for enantioselective phase transfer of chiral molecules, such as for separation of optical isomers.

A mixture of JNP10 nanoparticles in CHCl₃ was prepared by dispersing JNP10 in CHCl₃ at a concentration of about 0.15 mg/mL. Three aqueous solutions of alanine were also prepared by dissolving about 10 mmol of each of the D-alanine, L-alanine, and D,L-alanine in 100 mL of water. In three separate vials, an equal volume of the JNP10 mixture and one of the alanine solutions, namely, JNP10 with D-alanine solution, JNP10 with L-alanine solution, and JNP10 with D,L-alanine solution, were gently mixed for about 30 minutes.

The surface ligands of the JNP10, namely, C6SH and MPD, accounted for about 10% of the total nanoparticle mass, with approximately remaining 90% being gold. Amount of alanine dissolved in the solutions was about 100 times the amount of surface ligands to ensure that all of JNP10 nanoparticle ensembles were fully saturated by the alanine.

Figure 13:
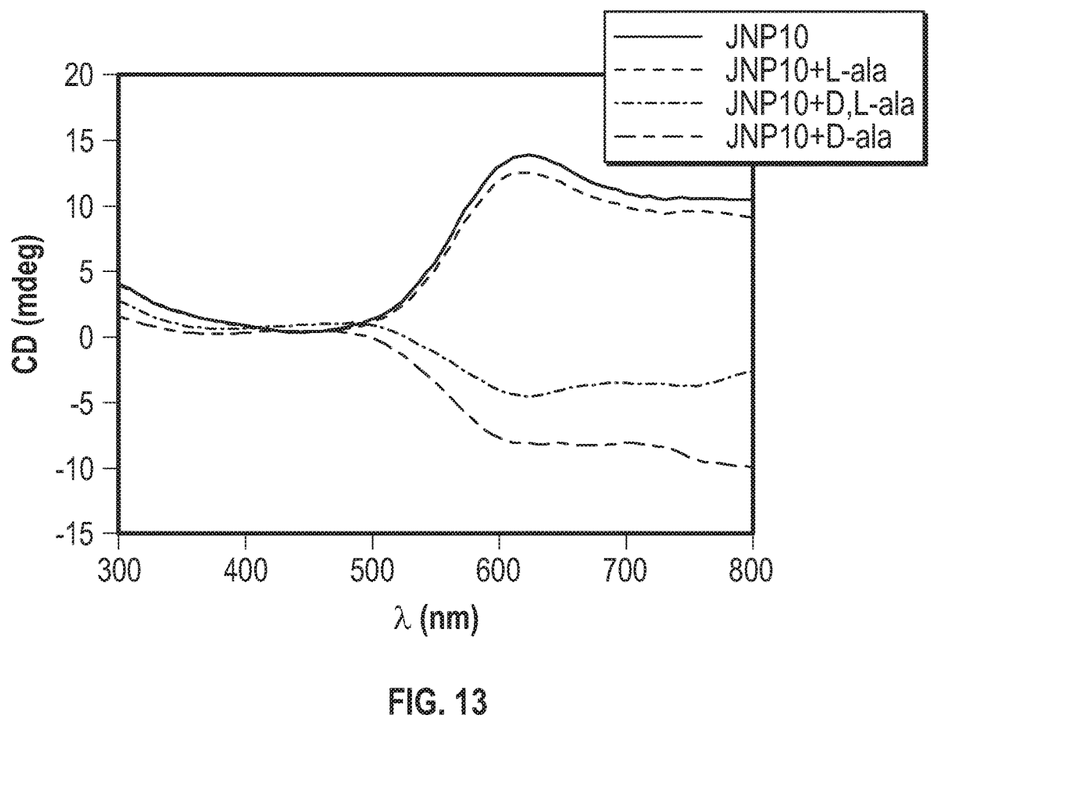
FIG. 13 is a plot of circular dichroism spectra of gold Janus nanoparticle ensembles with alanine according to an embodiment of the present disclosure.

A sample of each of the three JNP10 alanine mixtures and a control JNP10 mixture was placed into a 1 cm quartz cuvette, which was then subjected to CD measurements. With reference to FIG. 13, it was observed that JNP10 nanoparticles of the control mixture exhibited a PCD profile in CHCl₃ similar to that in H₂O before mixing with alanine as shown in FIGS. 9, 11, and 12 with a positive peak of about +13.9 mdeg at about 606 nm, suggesting that both micelle and reverse micelle-like structures of the Janus nanoparticles followed the same patterns of nanoparticle organization.

After mixing with L-alanine in water, CD measurements of the CHCl₃ layer showed virtually no change, indicating a lack of interactions between the JNP10 nanoparticles and L-alanine since peak intensity decreased only slightly to about +12.9 mdeg. Similarly, upon mixing with L-alanine, the CH₃Cl layer of JNP10 mixture showed no change in the UV-vis absorption profiles, also indicating no interaction between JNP10 and L-alanine.

The aqueous layers, namely, alanine solutions, showed no CD signal between about 500 nm and about 800 nm. The aqueous layer of L-alanine after mixing with JNP10 mixture showed a positive CD peak at about 218 nm, which is characteristic of L-alanine monomers. For the aqueous D-alanine layer, a negative CD peak was observed at about 222 nm. The aqueous layer of D, L-alanine did not generate a CD signal, indicating that there were no enantiomeric excess in the mixture.

However, mixing JNP10 nanoparticles with D-alanine led to a drastic change of the nanoparticle PCD response, as demonstrated by the CD peak becoming negative, about −8.3 mdeg. The CD signals of JNP10 mixture after mixing with D-alanine solution were reversed in sign between about 500 nm and about 800 nm, indicating a change of chirality. In addition, the UV-vis absorption profile of JNP10 mixture after mixing with D-alanine solution was blue-shifted with a lower intensity, which also suggested interaction between the JNP10 mixture with D-alanine solution. The chloroform layer of the JNP10 mixture after mixing with D, L-alanine solution showed similar profiles in both CD and UV-vis, as compared to the JNP10 mixture with the D-alanine solution, indicating selective interaction between JNP10 and D-alanine.

Since chiral structures are more likely to interact with molecules of opposite chirality, this PCD response demonstrates that the chirality of the JNP10 nanoparticle ensembles was equivalent to that of an L enantiomer of alanine. In addition, the change of the sign of the PCD signals upon interaction with D-alanine is due to the physical confinement of the D-alanine molecules within the nanoscale hollow interior of the JNP nanoparticle ensembles. In particular, D-alanine encapsulated by JNP nanoparticle ensembles behaved analogously to D-alanine crystals where negative CD absorption is generally observed and was further enhanced by JNP10 nanoparticle surface plasmon resonance.

The interaction between JNP10 nanoparticles and D enantiomers allows the JNP10 nanoparticles to be used for separation of D and L enantiomers. This was demonstrated by mixing JNP10 nanoparticles with the D,L-alanine solution, which resembles the PCD profile of the JNP10 nanoparticles being mixed with D-alanine, displaying a peak intensity of about −4.8 mdeg. The similarity between the two spectra, namely of the JNP10 nanoparticles with D-alanine and with D,L-alanine solutions demonstrates selective interaction of JNP10 nanoparticle ensembles with the D enantiomer but not with the L enantiomer.

It will be appreciated that of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, or material.

What is claimed is:

1. A method for processing an analyte, the method comprising:
    adding a plurality of amphiphilic nanoparticles to a solvent to form a mixture, wherein each amphiphilic nanoparticle of the plurality of amphiphilic nanoparticles includes a gold core having a first surface portion and a second surface portion, the first surface portion functionalized with 1-hexanethiolate and the second surface portion functionalized 3-mercapto-1,2-propanediol via interfacial ligand exchange reaction and the plurality of amphiphilic nanoparticles self-assemble into a plurality of enantioselective, vesicle-like nanostructures without assistance of a template or a scaffold;
    adding an analyte to the mixture to form an analyte mixture, wherein molecules of the analyte bind with the plurality of enantioselective, vesicle-like nanostructures;
    obtaining a test circular dichroism spectrum of the analyte mixture; and
    determining an enantiomeric property of the analyte based on a comparison of a baseline circular dichroism spectrum of the mixture to the test circular dichroism spectrum of the analyte mixture.

2. The method according to claim 1, further comprising:
    forming the plurality of amphiphilic nanoparticles, each of the plurality of amphiphilic nanoparticles includes a metallic core having a first surface portion and a second surface portion, the first surface portion including hydrophobic ligands and the second surface portion including hydrophilic ligands.

3. The method according to claim 2, wherein forming the plurality of amphiphilic nanoparticles includes:
    contacting a plurality of precursor nanoparticles each of which includes the metallic core with the hydrophobic ligands; and
    replacing a portion of the hydrophobic ligands with the hydrophilic ligands in a ligand-exchange reaction.

4. The method according to claim 3, wherein replacing the portion of the hydrophobic ligands with the hydrophilic ligands includes forming a monolayer of the precursor nanoparticles on a surface of a subphase and adding the hydrophilic ligands to the subphase.

5. The method according to claim 1, wherein the plurality of amphiphilic nanoparticles is added to a polar solvent.

6. The method according to claim 5, wherein the plurality of amphiphilic nanoparticles is added to the polar solvent selected from the group consisting of water, tetrahydrofuran, chloroform, and dichloromethane.

7. The method according to claim 1, further comprising separating L-form enantiomers of the analyte from D-form enantiomers of the analyte.

8. The method according to claim 7, wherein separating L-form enantiomers of the analyte from D-form enantiomers of the analyte includes binding one of the L-form enantiomers or the D-form enantiomers with the plurality of enantioselective, vesicle-like nanostructures.

9. The method according to claim 8, wherein separating L-form enantiomers of the analyte from D-form enantiomers of the analyte further includes removing the plurality of enantioselective, vesicle-like nanostructures bound to one of the L-form enantiomers or the D-form enantiomers from the mixture.

10. A kit for processing an analyte, the kit comprising:
a first reagent including a plurality of amphiphilic nanoparticles, each of the plurality of amphiphilic nanoparticles includes a gold core having a first surface portion and a second surface portion, the first surface portion functionalized with 1-hexanethiolate and the second surface portion functionalized 3-mercapto-1,2-propanediol via interfacial ligand exchange reaction; and a second reagent including a polar solvent, wherein upon adding the first reagent to the second reagent to form a mixture, the plurality of amphiphilic nanoparticles self-assemble into a plurality of enantioselective, vesicle-like nanostructures without assistance of a template or a scaffold, wherein the plurality of enantioselective, vesicle-like nanostructures are configured to bind with analyte molecules.

11. The kit according to claim 10, wherein the enantioselective, vesicle-like nanostructures have an average lateral dimension from about 50 nanometers to about 200 nanometers.

12. The kit according to claim 10, further comprising:
a baseline circular dichroism spectrum of the mixture having the plurality of enantioselective, vesicle-like nanostructures.

13. The kit according to claim 12, further comprising:
a third reagent including a second solvent for forming an analyte solution with an analyte.

14. The kit according to claim 13, further comprising instructions for:
mixing at least a portion of the mixture having the plurality of enantioselective, vesicle-like nanostructures with the analyte solution;
obtaining a test circular dichroism spectrum of the mixture with the analyte solution; and
determining an enantiomeric property of the analyte based on a comparison of the baseline circular dichroism spectrum of the mixture to the test circular dichroism spectrum.

* * * * *